United States Patent
Sanchez Nogue et al.

(10) Patent No.: US 12,281,346 B2
(45) Date of Patent: Apr. 22, 2025

(54) ADVANCED ANAEROBIC DIGESTION TO CARBOXYLIC ACIDS

(71) Applicants: Alliance for Sustainable Energy, LLC, Golden, CO (US); Colorado State University Research Foundation, Fort Collins, CO (US)

(72) Inventors: Violeta Sanchez Nogue, Manlleu (ES); Eric M. Karp, Denver, CO (US); Patrick Owen Saboe, Golden, CO (US); Lucas Hans Loetscher, Broomfield, CO (US); Sybil Sharvelle, Fort Collins, CO (US)

(73) Assignees: Alliance for Sustainable Energy, LLC, Golden, CO (US); Colorado State University Research Foundation, Fort Collins, CO (US)

( * ) Notice: Subject to any disclaimer, the term of this patent is extended or adjusted under 35 U.S.C. 154(b) by 323 days.

(21) Appl. No.: 17/306,251

(22) Filed: May 3, 2021

(65) Prior Publication Data
US 2021/0348201 A1 Nov. 11, 2021

Related U.S. Application Data

(60) Provisional application No. 63/020,598, filed on May 6, 2020.

(51) Int. Cl.
| | |
|---|---|
| C12P 7/40 | (2006.01) |
| B01D 61/24 | (2006.01) |
| B01D 63/02 | (2006.01) |
| B01D 71/26 | (2006.01) |
| C12P 7/52 | (2006.01) |
| C12P 7/54 | (2006.01) |
| C12P 39/00 | (2006.01) |

(52) U.S. Cl.
CPC ............ *C12P 7/40* (2013.01); *B01D 61/2461* (2022.08); *B01D 63/02* (2013.01); *B01D 71/261* (2022.08); *B01D 71/262* (2022.08); *C12P 7/52* (2013.01); *C12P 7/54* (2013.01); *C12P 39/00* (2013.01)

(58) Field of Classification Search
CPC .... C12P 39/00; C12P 7/54; C12P 7/52; C12P 7/40
See application file for complete search history.

(56) References Cited

U.S. PATENT DOCUMENTS 9,079,851 B2 * 7/2015 Gadewar .................. C07C 67/40
10,501,761 B2 * 12/2019 Medoff ..................... C08L 1/02

FOREIGN PATENT DOCUMENTS

| WO | WO-2008019941 A1 * | 2/2008 | ............. B01D 33/21 |
| WO | 2011/143169 A2 | 11/2011 | |
| WO | 2019/119157 A1 | 6/2019 | |
| WO | WO-2019160984 A1 * | 8/2019 | ............. C12M 21/12 |

OTHER PUBLICATIONS

Karunanithi, Sofiya, Ashish Kapoor, and Philip Delfino. "Separation of carboxylic acids from aqueous solutions using hollow fiber membrane contactors." Journal of Membrane Science and Research 5.3 (2019): 233-239. (Year: 2019).*
Sofiya, Ashish Kapoor, and Philip Delfino. "Separation of carboxylic acids from aqueous solutions using hollow fiber membrane contactors." Journal of Membrane Science and Research 5.3 (2019): 233-239. (Year: 2019).*
Kucka WO2008019941A1 machine translation (Year: 2023).*
Yang, S. T., et al. "Chapter 16: Extractive fermentation for the production of carboxylic acidsin: S.-t. Yang,(Ed.), Bioprocessing for value-added products from reneawable resources: New technologies and applications." (2007). (Year: 2007).*
Siddiqui, Muhammad Usama, Abul Fazal Muhammad Arif, and Salem Bashmal. "Permeability-selectivity analysis of microfiltration and ultrafiltration membranes: Effect of pore size and shape distribution and membrane stretching." Membranes 6.3 (2016): 40. (Year: 2016).*
Petronilho, A., A. Vivancos, and Martin Albrecht. "Ether formation through reductive coupling of ketones or aldehydes catalyzed by a mesoionic carbene iridium complex." Catalysis science & technology 7.23 (2017): 5766-5774. (Year: 2017).*
Alkaya et al., "Recovery of acids from anaerobic acidification broth by liquid-liquid extraction", Chemosphere, 2009, vol. 77, pp. 1137-1142.
Biddy et al., "The Techno-Economic Basis for Coproduct Manufacturing to Enable Hydrocarbon Fuel Production from Lignocellulosic Biomass", ACS Sustainable Chemistry & Engineering, 2016, vol. 4, pp. 3196-3211.
Blahušiak et al., "New approach to regeneration of an ionic liquid containing solvent by molecular distillation", Chemical Papers, 2011, vol. 65, No. 5, pp. 603-607.
Chamy et al., "Anaerobic monodigestion of poultry manure: determination of operational parameters for CSTR", Water Science & Technology, 2012, pp. 53-59.
Demirel et al., "Acidogenesis in two-phase anaerobic treatment of dairy wastewater", European Symposium on Environmental Biotechnology—ESEB Apr. 2004: Proceedings of the European Symposium on Environmental Biotechnology, pp. 439-442.
Griffin, "Anaerobic Digestion of Organic Wastes: The Impact of Operating Conditions on Hydrolysis Efficiency and Microbial Community Composition", Thesis—in Partial Fullfilment of the Requirements for the Degree of Master of Science, Colorado State University, Summer 2012, pp. 1-103.
Gu et al., "Propionic Acid Production by Extractive Fermentation. I. Solvent Considerations", Biotechonolgy and Bioengineering, Feb. 1998, vol. 57, No. 4, pp. 454-461.

(Continued)

*Primary Examiner* — Robert J Yamasaki
*Assistant Examiner* — Trevor Kane
(74) *Attorney, Agent, or Firm* — Michael A. McIntyre

(57) ABSTRACT

The present disclosure relates to a method that includes utilizing a microorganism for the converting of a substrate to an acid contained in a mixture that includes the acid and water, maintaining a pH of the mixture to less than 5, and treating the mixture with a first stream comprising an organic.

15 Claims, 11 Drawing Sheets

(56) References Cited

OTHER PUBLICATIONS

Harscoat et al., "Influence of Fermentation Conditions and Microfiltration Processes on Membrane Fouling During Recovery of GlucuronanePolysaccharides from Fermentation Broths", Biotechnology and Bioengineering, Dec. 1999, vol. 65, No. 5, pp. 500-511.
Hasan et al., "Volatile fatty acids production from anaerobic treatment of cassava wastewater. Effect of temperature and alkalinity", Environmental Technology, Apr. 2015, pp. 1-10.
Holtzapple et al., "Biomass Conversion to Mixed Alcohol Fuels Using the MixAlco Process", Applied Biochemistry and Biotechnology, 1999, vol. 77-79, pp. 609-631.
Hong et al., "Optimization of volatile fatty acid production with co-substrate of food wastes and dewatered excess sludge using response surface methodology", Bioresource Technology, 2010, vol. 101, pp. 5487-5493.
Huang et al., "Volatile fatty acids (VFAs) production from swine manure through short-term dry anaerobic digestion and its separation from nitrogen and phosphorus resources in the digestate", Water Research, 2016, vol. 90, pp. 344-353.
Huang et al., "A novel acetogenic bacteria isolated from waste activated sludge and its potential application for enhancing anaerobic digestion performance", Journal of Environmental Management, 2020, vol. 255, pp. 1-7.
Jaffrin, "Dynamic filtration with rotating disks, and rotating and vibrating membranes: An update", Current Opinion in Chemical Engineering, 2012, vol. 1, pp. 171-177.
Karim, "Digestion of High Solids Cattle Manure", Thesis—in Partial Fulfillment of the Requirements for the Degree of Master of Science, Colorado State University, Fall 2013, pp. 1-127.
Kertes et al., "Extraction Chemistry of Fermentation Product Carboxylic Acids", Biotechnology and Bioengineering, 1986, vol. XXVIII, pp. 269-282.
Keshav et al., "Back extraction of propionic acid from loaded organic phase", Chemical Engineering Science, 2010, vol. 65, pp. 2751-2757.
Kim et al., "Development of a Modified Three-Stage Methane Production Process Using Food Wastes", Applied Biochemistry and Biotechnology, 2000, vol. 84-86, pp. 731-741.
Kim et al., "Effect of Hydraulic Loading Rate on Acidogenesis in a Membrane-Coupled Anaerobic VFAs Fermenter", Environmental Technology, 2001, vol. 22, No. 1, pp. 91-99.
Kraemer et al., "Separation of butanol from acetone-butanol-ethanol fermentation by a hybrid extraction-distillation process", Computers and Chemical Engineering, 2011, vol. 35, pp. 949-963.
López-Garzón et al., "Recovery of carboxylic acids produced by fermentation", Biotechnology Advances, 2014, vol. 32, pp. 873-904.
Lee et al., "A review of the production and applications of waste-derived volatile fatty acids", Chemical Engineering Journal, 2014, vol. 235, pp. 83-99.
Li et al., "Volatile fatty acids distribution during acidogenesis of algal residues with pH control", World Journal of Microbiology & Biotechnology, 2013, vol. 29, pp. 1067-1073.
Loetscher, "The Development and Demonstration of a Multiple Stage Anaerobic Digester for the Treatment of High Solids Wastes", Thesis—in Partial Fulfillment of the Requirements for the Degree of Masters of Science, Colorado State University, Fall 2018, pp. 1-118.
Marták et al., "Density, Viscosity, and Structure of Equilibrium Solvent Phases in Butyric Acid Extraction by Phosphonium Ionic Liquid", Journal of Chemical & Engineering Data, 2017, vol. 62, pp. 3025-3035.
Méndez-Acosta et al., "Robust Control of Volatile Fatty Acids in Anaerobic Digestion Processes", Industrial & Engineering Chemistry Research, 2008, vol. 47, pp. 7715-7720.
Mendez-Acosta et al., "A robust control scheme to improve the stability of anaerobic digestion processes", Journal of Process Control, 2010, vol. 20, pp. 375-383.
Moretto et al., "An urban biorefinery for food waste and biological sludge conversion into polyhydroxyalkanoates and biogas", Water Research, 2020, vol. 170, pp. 1-12.
Nelson et al., "Mixed Carboxylic Acid Production by Megasphaera elsdenii from Glucose and Lignocellulosic Hydrolysate", Fermentation, 2017, vol. 3, No. 10, pp. 1-16.
Rahim et al., "Optimization of anaerobic digestion of sludge to produce volatile fatty acids", WIT Transactions on Ecology and The Environment, 2014, vol. 181, pp. 237-243.
Reyhanitash et al., "Recovery and conversion of acetic acid from a phosphonium phosphinate ionic liquid to enable valorization of fermented wastewater", Green Chemistry, 2019, vol. 21, pp. 2023-2034.
Saboe et al., "In situ recovery of bio-based carboxylic acids", Green Chemistry, 2018, vol. 20, pp. 1791-1804.
Salsali et al., "The effect of volatile fatty acids on the inactivation of Clostridium perfringens in anaerobic digestion", World Journal of Microbiology & Biotechnology, 2008, vol. 24, pp. 659-665.
Uludag-Demirer et al., "Volatile Fatty Acid Production from Anaerobic Digestion of Organic Residues", Microbial Lipid Production: Methods and Protocols, Methods in Molecular Biology, vol. 1995, Chapter 20, Springer Nature 2019, pp. 357-367.
Uribelarrea et al., "Anaerobic Digestion: Microbial and Biochemical Aspects of Volatile Acid Production", European Journal of Applied Microbiology and Biotechnology, 1981, vol. 12, pp. 118-122.
Vashishta, "Modular Spin Dish Filtration for Industrial and Municipal Applications", Chemical Engineering World, Jan. 2013, pp. 96-99.
Vasquez et al., "Biomass conversion to hydrocarbon fuels using the MixAlco™ process at a pilot-plant scale", Biomass and Bioenergy, 2014, vol. 62, pp. 138-148.
Wasewar et al., "Intensification of enzymatic conversion of glucose to lactic acid by reactive extraction", Chemical Engineering Science, 2003, pp. 3385-3393.
Yang et al., "Selective optimization in thermophilic acidogenesis of cheese-whey wastewater to acetic and butyric acids: partial acidification and methanation", Water Research, 2003, vol. 37, pp. 2467-2477.
Yang et al., "Optimizing volatile fatty acid production in partial acidogenesis of swine wastewater", Water Science and Technology, 2004, vol. 50, No. 8, pp. 169-176.
Yu et al., "Acidogenesis of dairy wastewater at various pH level", Water Science and Technology, 2002, vol. 45, No. 10, pp. 201-206.
Zech et al., "Membrane filtration based wastewater treatment", Chemical Technology, Jun. 2007, vol. 90, pp. 21-26.

* cited by examiner

A.

B.

A.

B.

C.

ADVANCED ANAEROBIC DIGESTION TO CARBOXYLIC ACIDS

CROSS-REFERENCE TO RELATED APPLICATIONS

This application claims priority from U.S. Provisional Patent Application No. 63/020,598 filed on May 6, 2020, the contents of which is incorporated herein by reference in their entirety.

CONTRACTUAL ORIGIN

This invention was made with government support under Contract No. DE-AC36-08GO28308 awarded by the Department of Energy. The government has certain rights in the invention.

BACKGROUND

Anaerobic digestion (AD) of biological wastes has the potential to produce valuable chemical compounds, including carboxylic acids such as volatile fatty acids (VFAs). However, current methods present significant technical barriers to commercialization. Therefore, there remains a need for improved methods and systems utilizing AD for the conversion of biomass to valuable products.

SUMMARY

An aspect of the present disclosure is a method that includes utilizing a microorganism for the converting of a substrate to an acid contained in a mixture that includes the acid and water, maintaining a pH of the mixture to less than 5, and treating the mixture with a first stream comprising an organic. The acid is present as a water-soluble species in the mixture, the treating results in the transferring of substantially all of the acid from the mixture to the first stream, the transferring results in the maintaining of the pH to less than 5, and the treating results in the forming of a water stream that is substantially acid-free and a second stream that includes the organic and the acid.

In some embodiments of the present disclosure, the substrate may include at least one of a food waste, an agricultural waste, and/or a municipal waste. In some embodiments of the present disclosure, the food waste may include diary waste. In some embodiments of the present disclosure, the agricultural waste may include manure. In some embodiments of the present disclosure, the microorganism may include a plurality of microorganisms. In some embodiments of the present disclosure, each microorganism of the plurality of microorganisms may be a naturally occurring microorganism.

In some embodiments of the present disclosure, the acid may include a carboxylic acid group attached to a hydrocarbon chain having between one and 20 carbon atoms. In some embodiments of the present disclosure, the acid may include at least one of formic acid, acetic acid, propionic acid, butyric acid, pentanoic acid, hexanoic acid, heptanoic acid, octanoic acid, nonanoic acid, and/or decanoic acid. In some embodiments of the present disclosure, the organic may include a phosphine oxide. In some embodiments of the present disclosure, the phosphine oxide may include Cyanex® 923 (a mixture of phosphine oxides). In some embodiments of the present disclosure, the pH may be between greater than 3 and less than 5.

In some embodiments of the present disclosure, the converting may be performed in at least one of a stirred tank reactor and/or a packed bed reactor. In some embodiments of the present disclosure, the method may further include, prior to the treating step, separating the microorganism from the mixture to produce an aqueous stream that is essentially solids free and containing at least a portion of the acid and a solids stream comprising the microorganism. In some embodiments of the present disclosure, the separating may be performed by at least one of filtration and/or centrifugation. In some embodiments of the present disclosure, the separating may be performed using a rotating ceramic disk filter.

In some embodiments of the present disclosure, the treating may be performed using a membrane having a thickness defined by a first side and a second side, the aqueous stream may be directed to the first side, the first stream may be directed to the second side, and the acid may be transferred through the thickness from the aqueous stream to the first stream to create the second stream and the water stream. In some embodiments of the present disclosure, the treating may be performed using a shell and tube separation unit. In some embodiments of the present disclosure, the method may further include recycling at least a portion of the water stream to the converting step. In some embodiments of the present disclosure, the method may further include separating the acid from the second stream to create a product stream comprising the acid. In some embodiments of the present disclosure, the separating of the acid may be performed by distillation.

BRIEF DESCRIPTION OF THE DRAWINGS

Some embodiments are illustrated in referenced figures of the drawings. It is intended that the embodiments and figures disclosed herein are to be considered illustrative rather than limiting.

Figure 1:
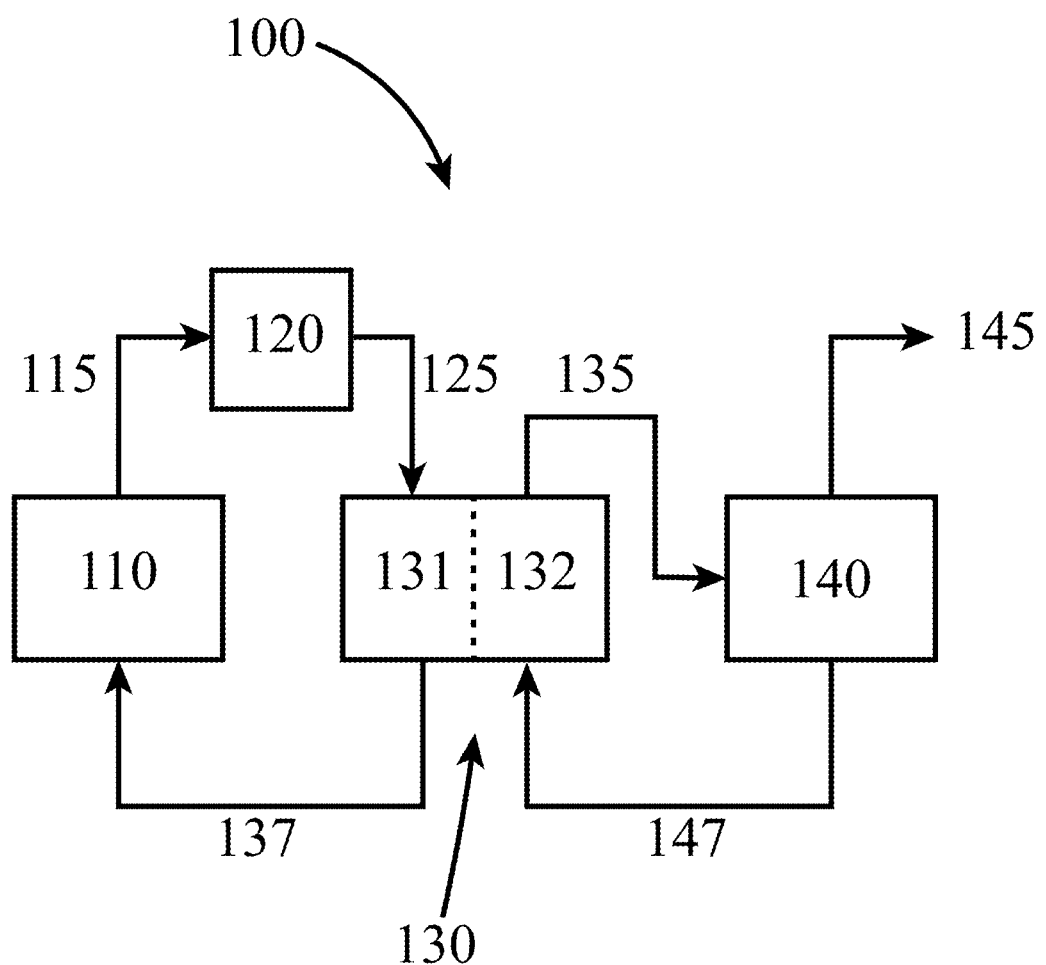
FIG. 1 illustrates a system for the continuous production of carboxylic acids, according to some embodiments of the present disclosure.

| REFERENCE NUMBERS |
| --- |
| 100 . . . system |
| 110 . . . bioreactor |
| 115 . . . fermentation stream |
| 120 . . . solids removal unit |
| 125 . . . permeate |
| 130 . . . extraction unit |
| 131 . . . aqueous phase |
| 132 . . . organic phase |
| 135 . . . second organic stream |
| 137 . . . aqueous stream |
| 140 . . . separation unit |
| 145 . . . carboxylic acid product stream |
| 147 . . . first organic stream |
| 200 . . . method |
| 210 . . . converting |
| 220 . . . removing |
| 230 . . . treating |
| 240 . . . separating |
| 250 . . . recycling |

DETAILED DESCRIPTION

The embodiments described herein should not necessarily be construed as limited to addressing any of the particular problems or deficiencies discussed herein. References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to +20%, +15%, +10%, +5%, or +1% of a specific numeric value or target. In some embodiments of the present invention, the term "about" is used to indicate an uncertainty limit of less than or equal to +1%, +0.9%, +0.8%, +0.7%, +0.6%, +0.5%, +0.4%, +0.3%, +0.2%, or +0.1% of a specific numeric value or target.

The present disclosure relates to systems and methods for the production of carboxylic acids, e.g., VFAs, resulting from, among other things, the non-sterile anaerobic digestion of waste feedstocks. In some embodiments of the present disclosure, carboxylic acids may be removed in situ before the microbiome used in an anaerobic digestion process can further convert the carboxylic acids to methane. A benefit of producing carboxylic acids (e.g., VFAs) is that VFAs are of higher value than methane and can be used as platform chemicals for the production of, among other things, fuels, chemicals, and/or polymer precursors. In some embodiments of the present disclosure, a system for producing VFAs may include passing anaerobic digestor media (e.g., from a bioreactor) through a solids removal unit (e.g., a rotating ceramic disk filter), followed by passing the permeate through an extraction unit where an organic phase, for example a phosphine oxide-based extractant (e.g., Cyanex® 923) preferentially removes the acidic components from the permeate. The acids may then be separated from the organic phase via a separation unit (e.g., distillation) as a substantially pure product. Such a system, therefore, may provide a means for the continuous removal of carboxylic acids from a bioreactor, thereby maintaining the pH of the fermentation media at a value that is low enough to both arrest the conversion at acidogenesis, but not so low as to impede the formation of carboxylic acids.

As described in more detail below, anaerobic digestion of waste, if not impeded, will normally convert all or most of a feedstock to biogas (i.e., methane) through a chemical pathway having four distinct steps: (1) hydrolysis, (2) acidogenesis, (3) acetogenesis, and (4) methanogenesis. Each step occurs sequentially and is thermodynamically downhill in energy from the previous step. Accordingly, the process may be driven continuously by the removal of the biogas from the system. However, biogas is of relatively low value. To produce higher value products, the present disclosure provides systems and methods that produce carboxylic acids in a continuous fashion by halting the chemical pathway in the second, acidogenesis step. More specifically, referring to FIGS. 1 and 2, and as described herein, the present disclosure relates to systems and methods that produce mostly carboxylic acids by stopping the progression of biomass conversion in step (2) in a bioreactor 110 (see FIG. 1) by controlling the pH of the fermentation mixture (i.e., media) to less than about 5. Maintaining the pH to less than about 5, as shown herein, allows the carboxylic acid-producing microorganisms to continue to thrive and produce, while the microorganisms more suited to acetogenesis and/or methanogenesis (i.e., the downstream steps in the chemical pathway) are effectively rendered inactive due to the low pH.

FIG. 1 illustrates a system 100 designed for the continuous production of carboxylic acids (e.g., VFAs) from the anaerobic digestion of waste feedstocks, according to some embodiments of the present disclosure. In this example, the system 100 may include a bioreactor 110 in which various waste feedstocks (i.e., substrates) are metabolized by microorganisms maintained in the bioreactor 110 to produce carboxylic acids, including VFAs. Examples of feedstocks that may be converted to carboxylic acids by the microorganisms include at least one of food waste, agricultural waste, municipal organics waste, fats, oils and greases, and/or food processing waste. More specific examples of feedstocks include dairy waste, manure, industrial, commercial, and residential food wastes, municipal sludges and biosolids, manure and manure slurries, and/or citrus waste. A bioreactor 110 may include at least one of a stirred-tank reactor and/or a fixed-bed reactor. In some embodiments of the present disclosure, a system 100, including a bioreactor 110 may be operated in a batch mode, a continuous mode, and/or a semi-continuous mode. For example, a fixed-bed bioreactor 110 may be charged with a batch of solid substrate containing at least one microorganism, after which, the system 100 is operated in a continuous fashion until substantially all of the solid substrate has been converted to carboxylic acids. In some embodiments of the present disclosure, the system 100 may be stopped to allow the solids in the fixed-bed bioreactor 110 and/or the microorganisms to be replaced with "fresh" feedstock and/or microorganisms, allowing the next batch to be performed. In some embodiments of the present disclosure, a stirred-tank bioreactor 110 may be operated such that carboxylic acids are produced continuously, with "fresh" feedstock and/or microorganisms replenished as needed. In some embodiments, a substrate may be provided that is biologically active, where "biologically active" refers to the substrate containing a microbial consortia capable of metabolizing the substrate and/or its degradation products to produce, among other things, carboxylic acids. A microbial consortia, as defined herein, refers to a group of different species of microorganisms that act together as a community; two or more groups of species living symbiotically.

In some embodiments of the present disclosure, a bioreactor 110 may be operated at a temperature between about 20° C. and about 60° C., at a solids concentration between about 1 wt % and about 30 wt %, and/or at a pH of less than about 5, or between about 2.5 and about 5. The pH in a bioreactor 110 may be controlled by the addition of a base and/or, as described in more detail below, by the continuous and/or batch removal of acids from the fermentation media, as they are produced.

Referring again to FIG. 1, in some embodiments of the present disclosure, at least a portion of the media may be continuously, or in a semi-continuous fashion, removed from the bioreactor 110. This fermentation stream 115 may include, among other things, a mixture of water, carboxylic acids, substrate, and/or microorganisms. To enable better downstream processing, such a fermentation stream 115 may be directed to a solids removal unit 120, configured to remove substantially all of the solids contained in the fermentation stream 115 to produce a substantially solids-free permeate 125. The solids (e.g., retentate, not shown) removed from the fermentation stream 115 may be recycled back to the bioreactor and/or disposed of. Solids may be removed from the fermentation stream 115 by a solids removal unit 120 including at least one of a filtration unit, a centrifugation unit, and/or an electrostatic unit. In some embodiments of the present disclosure, a solids removal unit 120 may include a filtration unit operation, such as at least one of a rotary disk filtration unit, a pressure filter, a filter press, and/or a vacuum filter. In some embodiments of the present disclosure, the solids removal unit 120 may include a rotary disc filter having a ceramic membrane. As described herein, a rotary disk filter may provide a high shear rate at the membrane surface, which retains cells and debris while providing a high throughput of sterile filtered (e.g., 0.2 um pore size) permeate containing VFAs. A rotary disk may be operated at between about 500 RPM and about 2000 RPM and at a transmembrane pressure between about 2 psi and about 150 psi. The ceramic membrane may be constructed of any suitable ceramic including $ZrO_2$ and/or $TiO_2$ and having an average pore size of about 0.2 μm. In addition, in some embodiments, a rotary disk filter may be operated at a temperature between about 20° C. and about 60° C., using a heating/cooling jacket.

The solids free permeate 125 from the solids removal unit 120, or at least substantially solids-free permeate, may then be directed to an extraction unit 130, to which a first organic stream 147 may also be directed. The first organic stream 147 may be substantially free of carboxylic acids, such that it has a high capacity to absorb carboxylic acids from the permeate 125. In some embodiments of the present disclosure, an extraction unit 130 may include a liquid-liquid extraction column where the aqueous permeate 125 is contacted with the first organic stream 147. As a result, at least a portion of the carboxylic acids may transfer from the aqueous permeate 125 into the first organic stream 147, resulting in an aqueous stream 137 that is substantially free of carboxylic acids, and a second organic stream 135 containing at least a portion of the carboxylic acids that were contained in the permeate 125. In some embodiments of the present disclosure, an extraction unit 130 may be divided into two sections divided by a membrane (dashed line). A first portion of an extraction unit 130 may provide a volume for the aqueous phase 131 created by the incoming permeate 125, and a second volume for the organic phase 132 created by the incoming first organic stream 147. A membrane may provide a barrier to the aqueous phase and any remaining solids, and preferentially allow only the carboxylic acids to diffuse from the permeate 125, through the membrane, into the first organic stream 147, resulting in the formation of the essentially carboxylic acid-free aqueous stream 137 and the carboxylic acid-rich second organic stream 135. In some embodiments of the present disclosure, an extraction unit 130 may be a shell-and-tube unit, where each tube is constructed of a membrane material. Membrane materials suitable for the present disclosure include hollow fiber polypropylene and/or polyethylene fibers with pore sizes between about 0.03 um and about 0.04 um. The membrane may be operated with a transmembrane pressure between about 1 psi and about 15 psi with the aqueous side being at greater pressure than the organic side. This arrangement can lessen the potential transfer of organic phase into the aqueous phase.

In some embodiments of the present disclosure, a first organic stream 147 may include a phosphine oxide based extractant, for example a trioctylphosphine oxide diluted in a diluent such as mineral oil and/or commercially available mixtures of alkyl phosphine oxides such as Cyanex® 923. Other extractants that may be used are those that selectively hydrogen bond to the acidic proton on carboxylic acids through a lone pair of electrons on the extractant group. Examples of extractants that operate this way are alkylamines such as trioctlyamine. In some embodiments of the present disclosure, the first organic stream 147 may be provided to the extraction unit 130 at a ratio between about 1:100 and about 1:1 of the first organic stream 147 to the permeate 125.

Referring again to FIG. 1, in some embodiments of the present disclosure, the aqueous stream 137 resulting from the removal of the carboxylic acids from the permeate 125 may be recycled to the bioreactor 110. The aqueous stream 137, due to the removal of the carboxylic acids, may have a pH that is significantly less acidic (i.e., higher) than the pH range (e.g., between about 2.5 and about 5) of the fermentation media contained in the bioreactor 110. As a result, the recycled aqueous stream 137 may provide fresh capacity for the additional production of carboxylic acids from as yet unreacted waste feedstock, thereby extending the duration of the reaction and maximizing conversion of the feedstock and the yield of carboxylic acids. In this fashion, in some embodiments of the present disclosure, the pH of the media contained in the bioreactor 110 may be controlled to a range between greater than about 2.5 and less than about 5.0 by carefully balancing the removal rate of carboxylic acids from the bioreactor with the microorganisms' carboxylic acid production rate.

The second organic stream 135 produced by the extraction unit 130 and containing the carboxylic acids may be subsequently directed to a separation unit 140 for separating the carboxylic acids from the organic extractant, resulting in the formation of a substantially pure first organic stream 147, which may then be recycled to the extraction unit 130, and a substantially pure carboxylic acid product stream 145. In some embodiments of the present disclosure, a separation unit 140 may include a distillation column, a flash drum, an adsorption unit, and/or a crystallization unit. Optimized ASPENplus modeling and laboratory results indicate that suitable flash distillation conditions for removing water and VFAs from the loaded Cyanex® 923 phase are a column pressure of about 0.16 atm and a temperature of about 230° C., using a column packed with an industrial demister installed at the top of the column.

Figure 2:
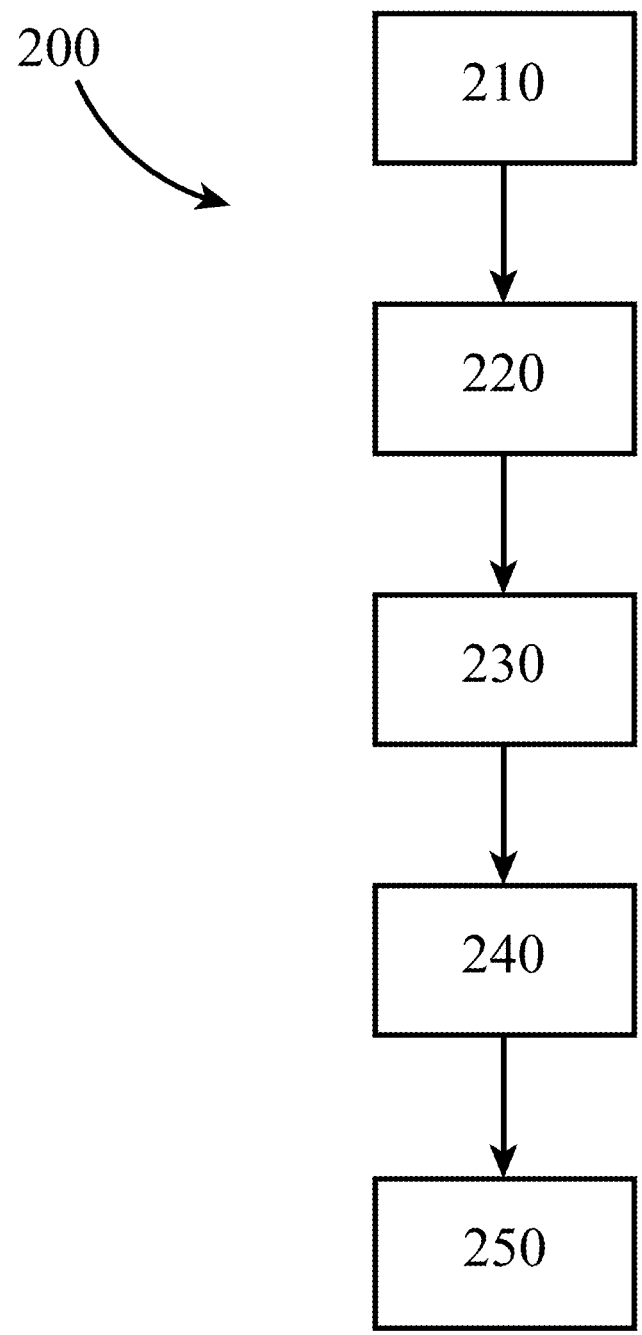
FIG. 2 illustrates a method for the continuous production of carboxylic acids, according to some embodiments of the present disclosure.

FIG. 2 provides a block diagram of a method 200 that enables the continuous production of carboxylic acids from an anaerobic fermentation process of various solid waste feedstocks. This exemplary method 200 begins with the converting 210 of the feedstock to carboxylic acids by one or more microorganisms, for example in a bioreactor, to produce a fermentation stream containing the carboxylic acids. This fermentation stream may then be directed to a unit operation configured for the removing 220 of any solids remaining in the carboxylic acid-rich fermentation stream, resulting in the forming of a permeate containing most of the carboxylic acids, and a separate solids stream. The removing 220 may be achieved, for example, by a filtration unit and/or centrifugation unit, where the removing 220 may remove any unreacted feedstock and or cell materials from the fermentation media to produce the permeate containing the carboxylic acids. The permeate may be subsequently directed to a unit operation for the treating 230 of the fermentation stream, resulting in the removal of at least a portion of the carboxylic acids from the fermentation stream. As described above, this treating 230 may be accomplished using an extraction unit (e.g., a shell-and-tube membrane separation unit) that contacts the permeate with an organic extracting agent (e.g., an organic phosphine material). As a result, at least a portion of the carboxylic acids may be transferred from the permeate to the organic stream, resulting in the forming of a clean aqueous stream that is substantially free of carboxylic acids, and an organic stream containing at least a portion of the carboxylic acids that were produced in the converting 210 step of the method 200. The relatively acid-free aqueous stream may then be directed back to the converting 210 step by the recycling 250 of the aqueous stream to the bioreactor. The carboxylic acid-rich organic stream may then be directed to a separating 240 step, such as a distillation unit, where the carboxylic acids are removed from the organic extracting agent to produce a substantially pure carboxylic acid stream and a substantially pure organic stream, which may be recycled to the treating 230 step (e.g., extraction unit). The purified carboxylic acids may be subsequently sold and/or upgraded to produce a variety of useful chemical intermediates and/or fuels.

Figure 3:
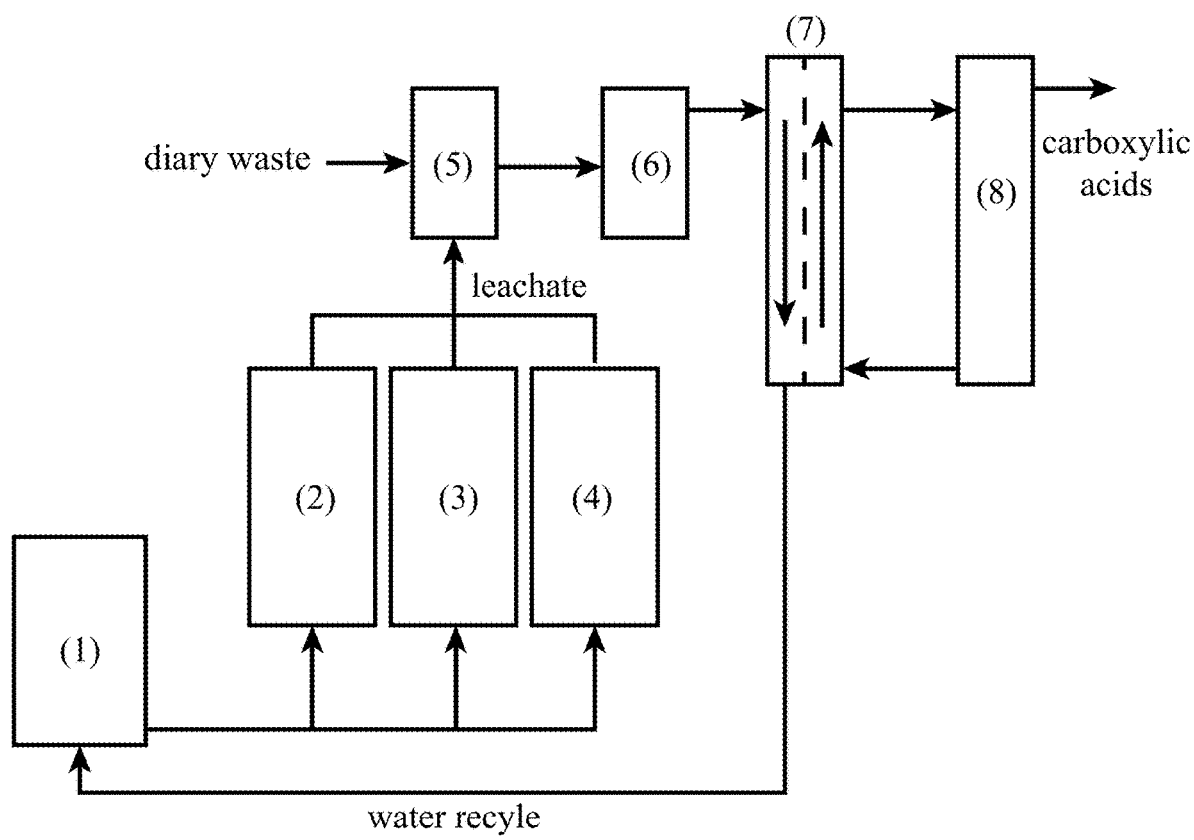
FIG. 3 illustrates a more detailed schematic of an exemplary system for the continuous production of carboxylic acids, according to some embodiments of the present disclosure. (1) Feed tank; (2-4) packed bed bioreactor with solid waste material such as, manure, food waste, municipal waste and/or lignocellulosic waste; (5) CSTR bioreactor containing low solids readily digestible waste (e.g., dairy waste); (6) Rotating Ceramic Disk filter (RCD) solids removal unit used as a cell and debris retention device; (7) Membrane Contacting Unit (MCU) extraction unit; and (8) Distillation column separation unit to recover neat carboxylic acids from an organic phase extractant.

As shown herein, some embodiments of an anaerobic digestion system for converting biomass feedstocks to carboxylic acids (e.g., VFAs) may function in high solids environments (between about 10 wt % and about 30 wt %), while operating at a relatively low pH (e.g., less than about 5), with carboxylic acid recovery steps that generate zero or minimal waste and has a very low energy footprint (e.g., less than 20% of the carboxylic acids' heating value). FIG. 3 illustrates a diagram of an exemplary system, according to some embodiments of the present disclosure. In this example, a bioreactor may include three "up flow solid state hydrolysis reactors" (UFSSHR) (elements (2-4)) where each unit may be packed with different solid waste materials. The waste placed in these bioreactors may have high solid contents, such as manure, food waste, organic municipal waste, and/or plant biomass waste. The bioreactors may be continuously operated at temperatures between about 35° C. and about 50° C. and water from a feed tank (1) may be circulated through them. In this example, the outlet stream of the UFSSHR's (2-4) may be a leachate containing mostly sugars and to a lesser extent VFAs. Since the pH of this solution may be low and the temperature of these solid waste bioreactors may be elevated, the low pH may aid in increasing the hydrolysis rate of the material by adding a chemical hydrolysis component in addition to the enzymatic hydrolysis taking place from the consortia of microorganisms contained in the bioreactors.

Referring again to FIG. 3, in some embodiments of the present disclosure, the UFSSHR effluent (e.g., leachate) may be directed to a second bioreactor, e.g., a continuous stirred tank reactor (CSTR) (element (5)) that may hold digestible low solids waste feedstock, for example waste dairy feedstock. In this example, the majority of the VFA production may occur in the CSTR bioreactor. In the CSTR, sugars liberated from the high solids waste material and from the dairy waste may undergo acidogenesis to form VFAs. Next, the VFAs and solid debris may be removed from the CSTR bioreactor to be directed to a solids removal unit. In some embodiments of the present disclosure, a solids removal unit may include a rotating ceramic disk (RCD) filter (element (6)). The pore size of the ceramic disk may be about 0.2 μm to retain cells and the disk may be constantly spinning (e.g., between about 1500 rpm and about 2400 rpm) to slough off debris and to maintain long operational times (on the order of months) before a cleaning cycle is performed. An RCD can operate continuously in solids environments up to about 30 wt %, and in low pH environments, making the device an ideal solution in this advanced anaerobic digestion system to continuously retain solids and cells.

Referring again to FIG. 3, the solids obtained from the solids removal unit (6) may be recycled back to the feed tank and a purge valve may collect some of the microorganism to be used as inoculate when replacing feedstock in future batches. The permeate resulting from the solids removal unit may contain water and a mixed slate of VFA products. The VFAs and water permeate may then be directed to an extraction unit (7), for example the shell side of a hollow fiber membrane contacting unit. In some embodiments of the present disclosure, a commercial phosphine oxide liquid extractant (e.g., Cyanex® 923) may be circulated on the tube side of a hollow fiber contactor. The liquid extractant may selectively extract VFAs through, among other things, hydrogen bonding to the acidic proton on the carboxylic acid group via Lewis acid-base pairing. The extracted VFAs may be subsequently recovered from the organic phase as a neat, water free carboxylic acid product via distillation (see FIG. 3, element (8)) where VFAs are stripped from the organic phase and recovered in the distillation column's overhead product. The high boiling point (B.P. ~400° C.) of the organic extractant may result in it being recovered in the distillation column's bottoms product, enabling its recovery and allowing it to be recirculated back to the extraction unit for continuous VFA extraction from the permeate. The mixed slate of VFAs collected from the distillation column's overhead may then be, among other things, ketonized and condensed via an etherification reaction, to produce diesel range fuels. Additionally, ethyl ester solvents may be produced in situ within the distillation column with the addition of an alcohol and acid catalyst. On the aqueous side of the membrane the pH of the water may be near neutral because the VFAs have been extracted. Thus, this aqueous stream may then be recycled back to the feed tank (1) of FIG. 3 and/or to the bioreactors (2-4). In some embodiments of the present disclosure, a purge valve may allow a small amount of water to leave the system if needed.

The VFAs produced from the embodiments described herein may include linear chain C2-C6 carboxylic acids produced at a pH of less than about 5. In some embodiments of the present disclosure, such carboxylic acids may be upgraded catalytically to diesel blendstocks. In some embodiments of the present disclosure, the anaerobic digestion systems described herein may separate these mixed C2-C6 or C2-C10 VFAs as an overhead product of a distillation column, containing <5% water from the distillation of the loaded organic phase with an energy footprint <20% of the heating value of the VFAs. In some embodiments of the present disclosure, these VFAs may then be ketonized over a ceria composite catalyst in the vapor phase to achieve C5-C15 linear chain ketones, which may then be etherified in the homogeneous or heterogeneous phase to produce C10-C30 ethers as a diesel blendstock. In addition to diesel blendstocks, the VFAs may be esterified in the distillation column to produce a mixed ester product (discussed below) that may be directly recovered in the distillation column's overhead product. The mixed ethyl esters may be used as fuel additives or as high value "green solvent" co-products.

Figure 4:
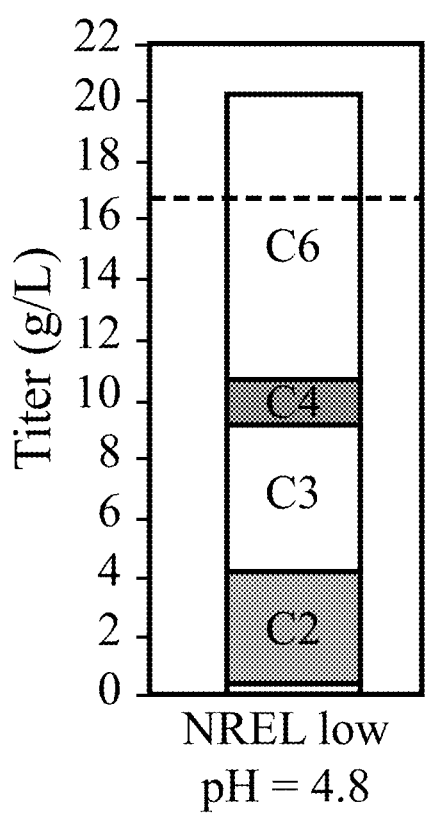
FIG. 4 illustrates in Panel (A) volatile fatty acid (VFA) titers obtained from low pH conditions in a semi-continuous fermentation, and in Panel (B) the corresponding wt % breakdown of VFA's produced, according to some embodiments of the present disclosure.
Figure 4:
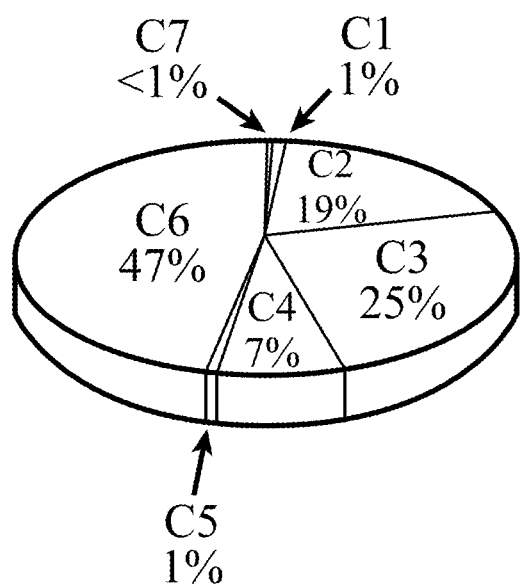

Panel A of FIG. 4 displays data collected from a semi-continuous culture, according to some embodiments of the present disclosure. Iodoform was initially added to the culture to chemically arrest methanogenesis. In practice, as described herein, the systems may be integrated to remove VFAs in situ and arrest methanogenesis via pH control, without iodoform. The data in Panel A of FIG. 4 show that a titer of ~21 g/L of mixed VFAs can be obtained at a pH of 4.8 with the microbial consortia used in these experiments. The measured ratios of VFA products obtained from these experiments are summarized in Panel B of FIG. 4. The measured wt % breakdown of VFA products were 1% formic acid (C1), 19% acetic acid (C2), 25% propionic acid (C3), 7% butyric acid (C4), 1% pentanoic acid (C5), and 47% hexanoic acid (C6).

Figure 5:
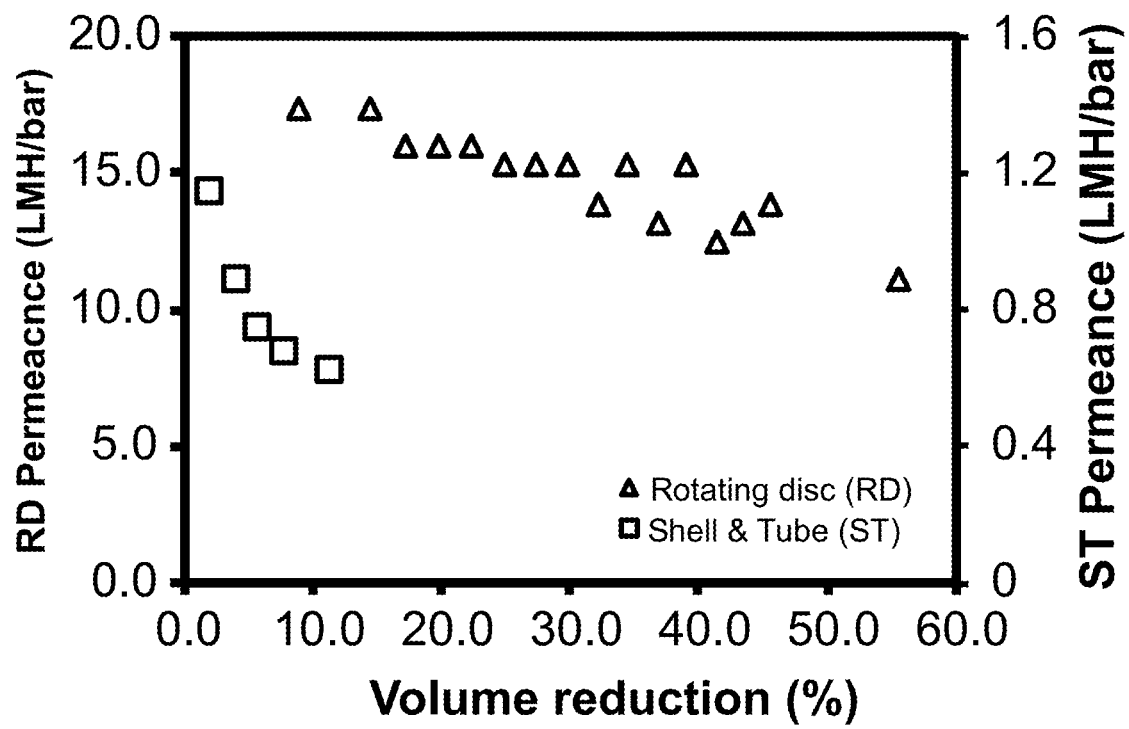
FIG. 5 illustrates in Panel (A) measurements of membrane permeance of the RCD filter compared to a conventional tangential flow shell and tube filtration device; in Panel (B) an image of the recovered solids free fermentation stream and stream containing the removed solids; and in Panel (C) an image of the disk after the filtration experiment, according to some embodiments of the present disclosure.
Figure 5:
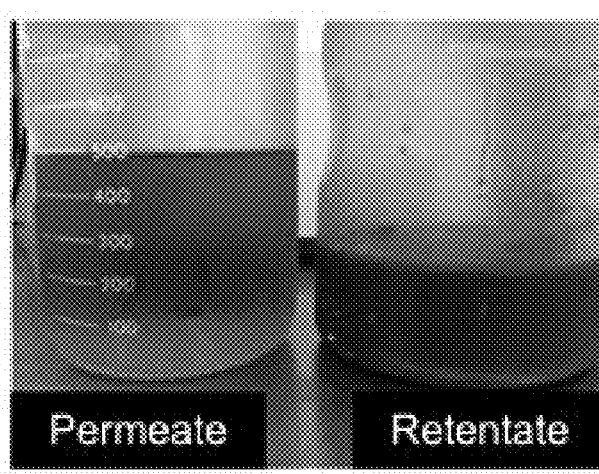
Figure 5:
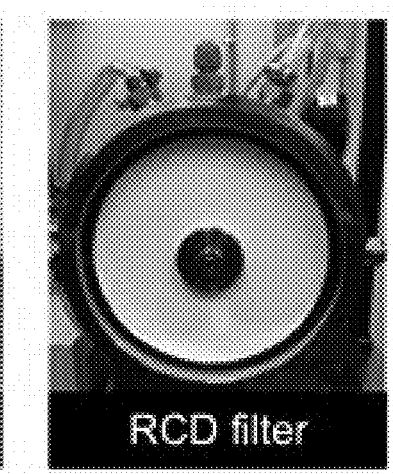

Regarding the solids separation unit, an RCD was tested for the filtering of AD sludge from the low pH experiment summarized in FIG. 4. FIG. 5 shows the results of sterile filtering the AD sludge with an RCD filter using a 0.2 μm ceramic filter. The results shown in Panel A of FIG. 5 demonstrate that an RCD unit can filter AD sludge with a permeance ~21× greater than a traditional shell and tube tangential flow filtration unit and is able to achieve ~55% volume reduction of the solution in only 10 minutes of filtration time, while losing only ~27% of its permeance (which is 18× higher than a shell and tube tangential flow filtration unit). Panel B of FIG. 5 shows the filtered permeate compared to the recovered retentate (i.e., solid-containing phase). The retentate contains a thick layer of sand like sludge at the bottom. Panel C of FIG. 5 shows an image of the disk after the filtration experiment. The disk appears essentially unfouled and demonstrates its effectiveness as a solids removal unit in continuous VFA production systems, as described herein. Given that the captured solids may be recirculated back to the bioreactor(s), volume reductions during filtration are not expected and it seems reasonable to expect that an RCD filtration unit will be able to maintain long, uninterrupted operational times and high fluxes during continuous operation. However, a cleaning cycle may be needed at some point during continuous operation. A cleaning cycle may be achieved using a 10 to 20 bar backflush with pure water. In some instances, a backflush with a 2N to 4N NaOH solution may be used. A backflush may be performed for a period of time between 1 hour and 2 hours and may be achieved offline during cleaning.

Initial experimental results show that Cyanex® 923, a phosphine oxide extractant, can effectively extract VFAs from the permeate (e.g., after filtration has removed solids). Specifically, data show that at a pH of about 4.8, about 74% of the total mass of VFAs from a permeate were extracted by Cyanex® 923. Hexanoic acid, pentanoic acid, and butyric acid were completely extracted from the solids-free bioreactor media and 52% of the propionic acid, and 37% of the acetic acid were also extracted from the permeate. This resulted in a total extracted amount of VFAs of 74% on a mass basis from the permeate on a single pass.

Figure 6:
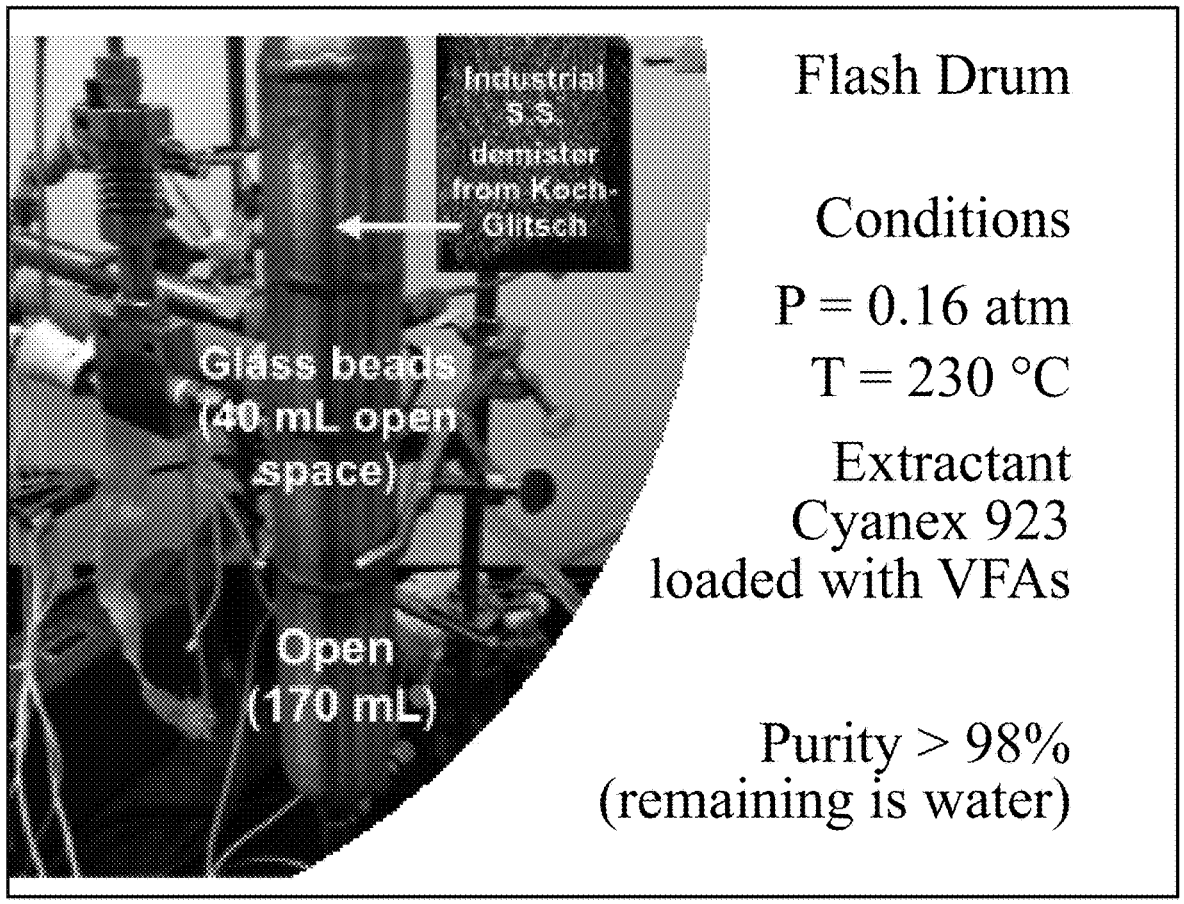
FIG. 6 illustrates a flash distillation unit constructed for the recovery of VFA's from a loaded organic phase, according to some embodiments of the present disclosure.

FIG. 6 shows an exemplary flash distillation unit that successfully removed C2-C6 VFAs from the organic phase produced by the extraction step. This exemplary flash distillation unit was constructed with three sections. The lowest section was 170 mL of open volume to collect the Cyanex® 923 in the bottoms stream as the high-boiling component. The next section was packed with glass beads leaving 40 mL of open space for vapors to travel to the final upper section of the flash column. The final upper section of the flash column was packed with an industrial de-mister material from Koch-Glitsch®, a corrugated metal similar to steel wool, and served to keep any high boiling Cyanex® 923 from passing into the overhead. Experiments using this custom flash distillation unit matched modeling data, with VFAs recovered in the distillation column's overhead stream at a purity of greater than 98% with the balance being a small amount of co-extracted water. The operating conductions used in this exemplary flash distillation column included a pressure of 0.16 atm and a temperature of 230° C. These conditions appear optimal given the high purity of the overhead product that was recovered.

concentration of 48 mg/L. Serum bottles were incubated at 32° C., and agitated at 100 rpm. VFA profiles were quantified by HPLC.

Figure 7:
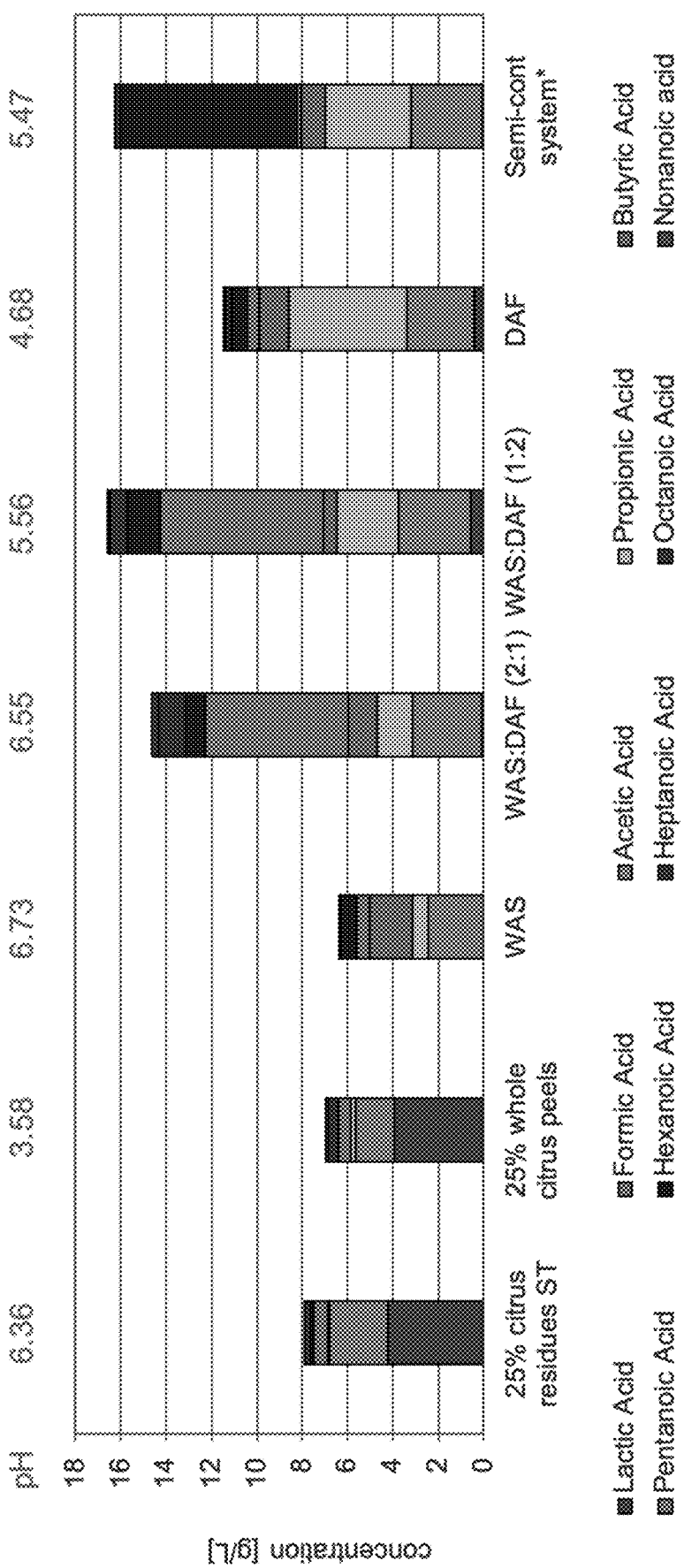
FIG. 7 illustrates final carboxylic acid profiles and pH obtained using different waste streams, according to some embodiments of the present disclosure.

Bioconversion: The different waste streams were evaluated in batch mode using serum bottles under anaerobic conditions. Samples for VFA analysis were taken regularly and pH was monitored over time. Interestingly, the acid profile obtained for the different substrates was notably different despite using the same microbial inoculum. In the case of the citrus waste streams, lower levels of acids were obtained (less than 8 g/L), with lactic acid being the predominant one, followed by acetic acid. These substrates exhibited a low buffering capability and the final pH was around 3.6. In the case of the waste streams from a cheese production facility's WWTP, higher levels of acids were produced especially when WAS and DAF streams were combined. With these substrates, the levels of lactic acids were drastically reduced, with pentanoic, acetic, and propionic acids being the major contributors (see FIG. 7). Acid compositions of the different substrates and blends are presented in Table 1.

TABLE 1

Acid composition of the different waste streams and blends.

| Substrate | $C_3H_6O_3$ | $C_2H_4O_2$ | $C_3H_6O_2$ | $C_4H_8O_2$ | $C_5H_{10}O_2$ | $C_6H_{12}O_2$ | $C_7H_{14}O_2$ | $C_8H_{16}O_2$ | $C_9H_{18}O_2$ |
|---|---|---|---|---|---|---|---|---|---|
| 25% citrus residues ST | 0.53 | 0.33 | 0.01 | 0 | 0.08 | 0.02 | 0.03 | 0 | 0 |
| 25% whole citrus peels | 0.56 | 0.25 | 0.03 | 0 | 0.08 | 0 | 0.06 | 0 | 0.02 |
| WAS | 0 | 0.38 | 0.11 | 0.30 | 0.09 | 0.11 | 0 | 0 | 0 |
| WAS:DAF (2:1) | 0 | 0.21 | 0.11 | 0.09 | 0.43 | 0.06 | 0.08 | 0.02 | 0 |
| WAS:DAF (1:2) | 0.03 | 0.19 | 0.17 | 0.03 | 0.43 | 0.09 | 0.05 | 0.01 | 0 |
| DAF | 0.04 | 0.26 | 0.46 | 0.11 | 0.04 | 0.06 | 0.02 | 0.01 | 0 |
| Semi-cont system | 0 | 0.19 | 0.23 | 0.07 | 0.01 | 0.48 | 0.01 | 0 | 0 |

Additional experimental results are described below. Four different waste streams were used to evaluate VFA production, including two different types of citrus wastes and two form a waste-water treatment plant (WWTP) of a cheese production facility. A Waste Activated Sludge (WAS) from a WWTP's primary treatment and the DAF stream from a Dissolved Air Floatation (DAF) system were tested individually and blended at ratios of 1:2 and 2:1 to determine possible synergistic effects. Serum bottles were prepared at an initial volume of 150 mL of substrate and using 10% (v/v) of activated sludge form our semi-continuous bioreactor system as a microbial inoculum. Methanogenesis was chemically inhibited by addition of iodoform at a final VFA Extraction Equilibrium: Previous work showed that the VFA extract composition can be predicted using multiple linear equations that model the extraction equilibrium. This mathematical model and the equations within, which can be found on GITHUB (https://github.com/NREL-SEPCON/LLE_Model_ISPR), uses a MATLAB interface for calculating the extract composition. Below, the acid profile and titer from multiple different substrates was used as input values for this extraction equilibrium model. The extract composition for each substrate is listed in Table 2. Here, the extract was assumed to contain Cyanex® 923, an effective extractant that binds to VFAs with a volume ratio of 10:1 aqueous to organic. Note that lactic and formic acid were not included in the model because of their known low partition coefficient into the organic phase.

TABLE 2

Organic phase concentrations of acids for various substrates

| | Titer | Conc. in ORG phase [g/L] | | | | | |
|---|---|---|---|---|---|---|---|
| Substrate | pH | (g/L) | $C_2H_4O_2$ | $C_3H_6O_2$ | $C_4H_8O_2$ | $C_5H_{10}O_2$ | $C_6H_{12}O_2$ | Total |
| 25% citrus residues ST | 3.63 | 3.44 | 8.60 | 0.54 | 0.00 | 6.07 | 1.47 | 16.67 |
| 25% whole citrus peels | 3.58 | 2.49 | 5.83 | 1.43 | 0.00 | 5.50 | 0.00 | 12.75 |
| WAS | 6.73 | 6.31 | 0.01 | 0.02 | 0.15 | 0.23 | 0.48 | 0.90 |

TABLE 2-continued

Organic phase concentrations of acids for various substrates

| Substrate | pH | Titer (g/L) | Conc. in ORG phase [g/L] | | | | | |
|---|---|---|---|---|---|---|---|---|
| | | | $C_2H_4O_2$ | $C_3H_6O_2$ | $C_4H_8O_2$ | $C_5H_{10}O_2$ | $C_6H_{12}O_2$ | Total |
| WAS:DAF (2:1) | 6.55 | 13.07 | 0.02 | 0.04 | 0.09 | 2.11 | 0.52 | 2.78 |
| WAS:DAF (1:2) | 5.56 | 15.14 | 0.18 | 0.81 | 0.41 | 19.55 | 5.94 | 26.89 |
| DAF | 4.68 | 10.71 | 3.69 | 21.53 | 8.28 | 4.66 | 6.78 | 44.94 |
| Semi-continuous system | 5.0 | 16.2 | 0.9 | 5.0 | 2.9 | 1.2 | 60.6 | 70.6 |

Figure 8:
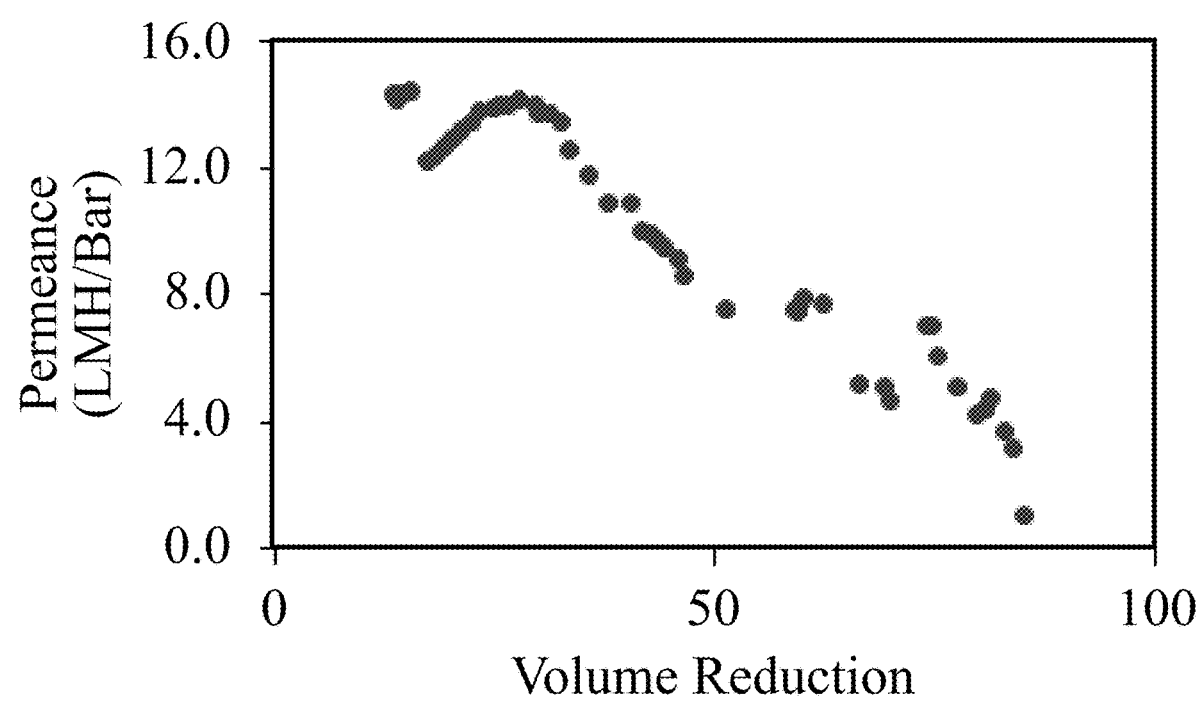
FIG. 8 illustrates permeance for an RCD filter as a function of volume reduction (0.5 corresponds to a 50% reduction in volume), according to some embodiments of the present disclosure. Previously, a shell-a-tube configuration was used to filter solids from the fermentation media, however, the permeance was much less (approximately 15-fold) compared to the RCD filter.

Filtration of AD Media: Cell and solids filtration from the AD broth was demonstrated by using a rotating disc ceramic membrane. Actual AD broth from a semi-continuous bioreactor was used as the starting material and the VFA concentration was adjusted to the titers shown in FIG. 7. Filtration of AD broth was completed using a rotating disc ceramic membrane setup (DCF152, Andritz, Germany). A photo of the unit is shown in Panel C of FIG. 5. The system pressure limitation was 10 bar and a heater/cooler was integrated with the system to control the process temperature. 3.5 liters of AD material was used as the feed. The system was pressurized to 50 psig and 3 liters of permeate were collected before the filtration was stopped. The rotational speed of the disc was set to 1200 rpm. The permeance of broth was calculated as a function of the volumetric reduction of the feed material (see FIG. 8). Note that the system hold-up was about 400 mL, meaning that a volumetric reduction was always less than 100% for this filtration system. A ceramic disc membrane with a nominal cut-off of 0.2 microns was used (the white disc in Panel C of FIG. 5). A photo of the permeate and retentate is shown in Panel B of FIG. 5.

Figure 9:
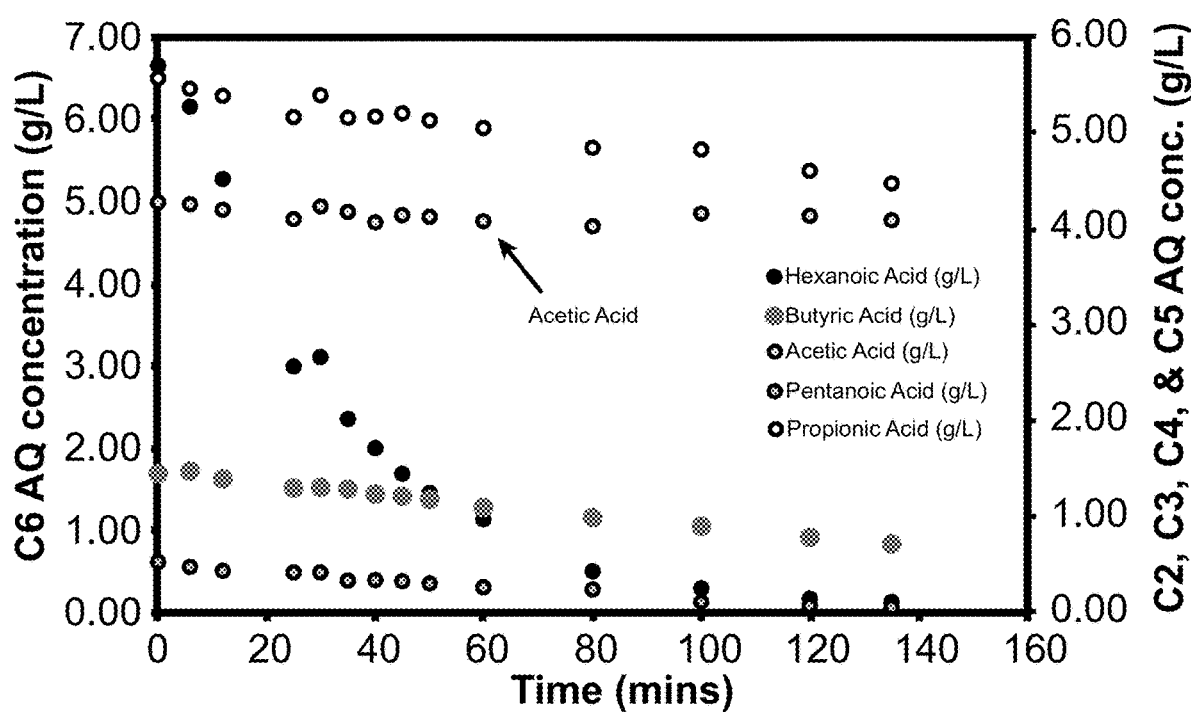
FIG. 9 illustrates VFA composition as a function of time during flow extraction with a Liqui-Cel hollow fiber membrane contactor (i.e., extraction unit), according to some embodiments of the present disclosure. The initial rate of hexanoic acid was calculated based on the first 30 minutes of extractions. VFAs C2-C5 displayed linear extraction behavior over 2 hours of extraction and thus their extraction rate was calculated over 2 hours.
Figure 10:
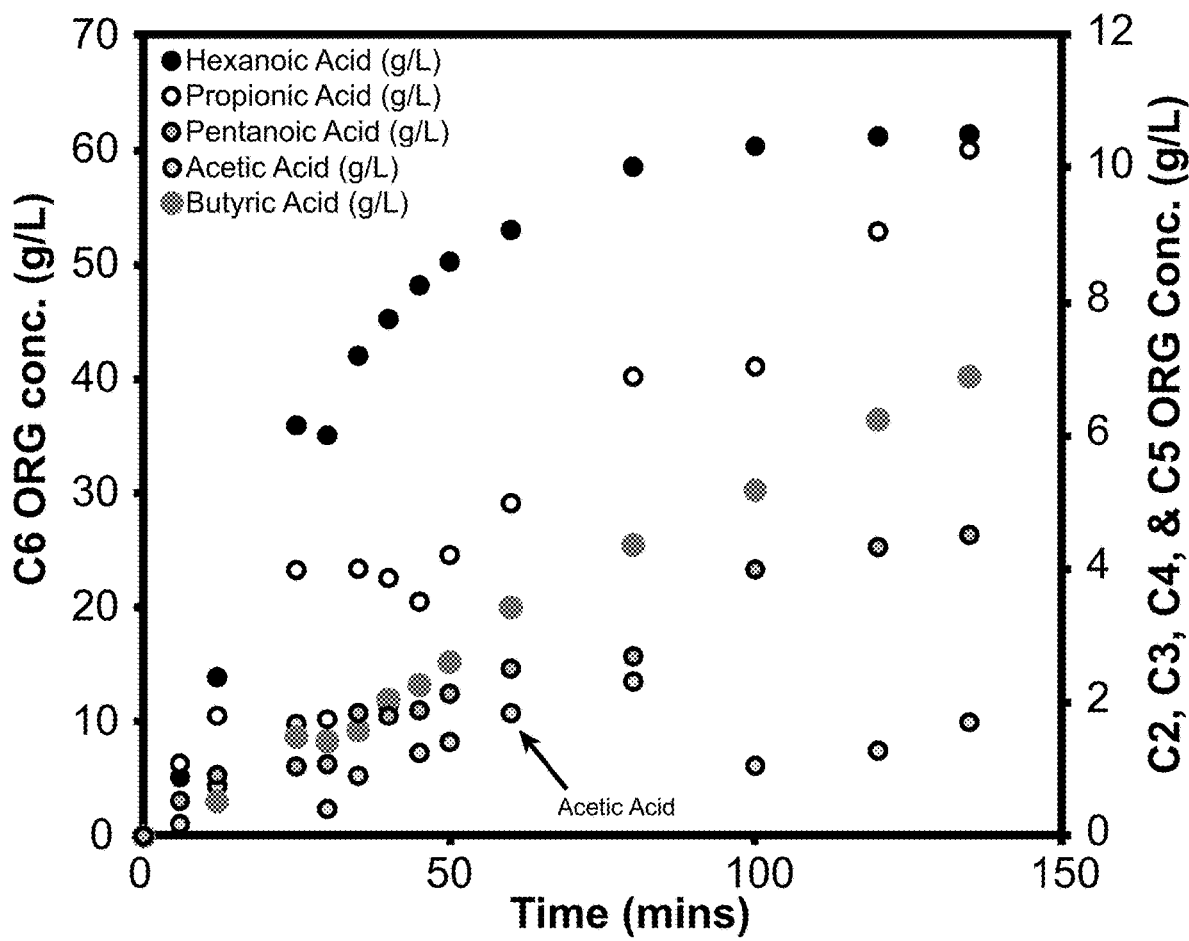
FIG. 10 illustrates the organic extractant phase (Cyanex® 923) profile of C2-C6 VFAs over 2 hours of extraction with a Liqui-Cel hollow fiber contactor (i.e., extraction unit), according to some embodiments of the present disclosure.
Figure 11:
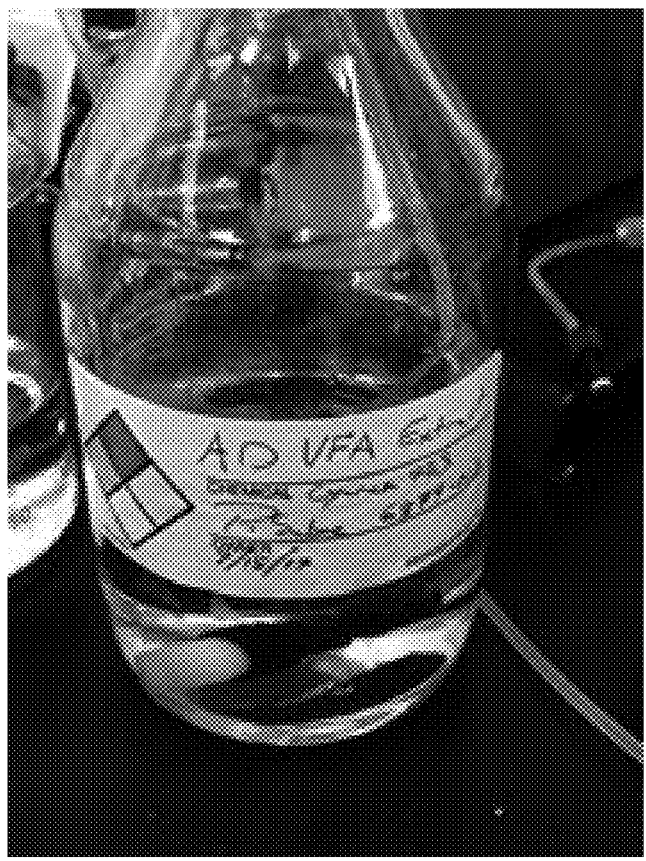
FIG. 11 illustrates VFA extract obtained from a shell-and-tube extraction unit containing 1.7 g/L acetic acid, 10.3 g/L propionic acid, 6.89 g/L butyric acid, 4.5 g/L pentanoic acid, and 61.4 g/L hexanoic acid (84.7 g/L total VFAs) in Cyanex® 923, according to some embodiments of the present disclosure.

Flow Extraction: The rate of VFA extraction was determined below to size an extraction system capable of extracting VFAs at a rate equal to the productivity of the bioreactor. The rates of extraction were measured using Cyanex® 923 (Cytec Inc., Woodland Park, NJ) and a Liqui-Cel membrane (2.5×8) contactor (3M, Maplewood, MN). The aqueous flow rate was set to 200 mL/min and the organic flow rate was set to 100 mL/min. The initial adjusted concentration of VFAs in the broth was 4.3 g/L acetic acid, 5.6 g/L propionic acid, 1.5 g/L butyric acid, 0.5 g/L valeric acid, 6.7 g/L caproic acid. The volume of the aqueous phase was 3.6 L and the volume of the organic phase was 0.36 L (thus the volume ratio between the aqueous and organic phase was 10:1 as used in the MATLAB model). The final pH was 4.4. The VFA profile over extraction time is shown below in FIG. 9. The organic phase composition of VFAs is shown in FIG. 10. The rates of extraction were 1.0 g acetic acid/(hr m$^2$), 2.3 g propionic acid/(hr m$^2$), 1.0 g butyric acid/(hr m$^2$), 0.7 g pentonic acid/(hr m$^2$), 13.7 g hexanoic acid/(hr m$^2$). When these rates were normalized to the initial titer, the trend of extraction rate increased as the chain length of the VFA increased. The normalized extraction rates (on a per g/L basis) are 0.24, 0.41, 0.72, 1.4, and 3.2 for C2-C6 VFAs respectively. A photo of the final extract is shown in FIG. 11.

Whether or not a reactant or product described herein is "bioderived" may be determined by analytical methods. Using radiocarbon and isotope ratio mass spectrometry analysis, the biobased content of materials can be determined. ASTM International, formally known as the American Society for Testing and Materials, has established a standard method for assessing the biobased content of carbon-containing materials. The ASTM method is designated ASTM-D6866. The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present-day radiocarbon and fossil carbon (containing no radiocarbon), then the pMC value obtained correlates directly to the amount of biomass material present in the sample. Thus, ASTM-D866 may be used to validate that the compositions described herein are and/or are not derived from renewable sources.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:
1. A method comprising:
   converting, utilizing a microorganism, a substrate into a carboxylic acid contained in a fermentation stream comprising the carboxylic acid, water, and solids;
   removing the solids from the fermentation stream to form a substantially solids-free permeate comprising the carboxylic acid and water;
   treating the permeate with a first stream comprising a phosphine oxide by directing the permeate to a first side of a membrane having a thickness defined by a first side and a second side, and directing the first stream to the second side of the membrane; and maintaining a pH of the permeate between greater than 2.5 and less than 5 without the addition of an acid or a base; wherein:

a concentration of the solids in the fermentation stream is between greater than 12 wt % and less than or equal to 30 wt %, the removing is performed using a rotating ceramic disk filter, the treating is performed using a volumetric ratio of the permeate to the first stream between 1:100 and 1:10, the carboxylic acid is present as a water-soluble species in the permeate, the treating results in the transferring of the carboxylic acid from the permeate, through the membrane thickness, to the first stream, the transferring results in the maintaining of the pH range, the treating results in the forming of a water stream and a second stream comprising the phosphine oxide and the carboxylic acid, and the membrane is not a hollow fiber membrane.

2. The method of claim 1, wherein the substrate comprises at least one of a food waste, an agricultural waste, or a municipal waste.

3. The method of claim 2, wherein the food waste comprises dairy waste.

4. The method of claim 2, wherein the agricultural waste comprises manure.

5. The method of claim 1, wherein the microorganism comprises a plurality of microorganisms.

6. The method of claim 5, wherein each microorganism of the plurality of microorganisms is a naturally occurring microorganism.

7. The method of claim 1, wherein the carboxylic acid comprises a carboxylic acid group attached to a hydrocarbon chain having between one and 20 carbon atoms.

8. The method of claim 7, wherein the carboxylic acid comprises at least one of formic acid, acetic acid, propionic acid, butyric acid, pentanoic acid, hexanoic acid, heptanoic acid, octanoic acid, nonanoic acid, or decanoic acid.

9. The method of claim 1, wherein the converting is performed in at least one of a stirred tank reactor or a packed bed reactor.

10. The method of claim 1, wherein the removing is performed by at least one of filtration or centrifugation.

11. The method of claim 1, further comprising recycling at least a portion of the water stream to the converting step.

12. The method of claim 1, further comprising separating the carboxylic acid from the second stream to create a product stream comprising the carboxylic acid.

13. The method of claim 12, wherein the separating of the carboxylic acid is performed by distillation.

14. The method of claim 1, wherein the membrane comprises polyethylene fibers with pore sizes between 0.03 um and 0.04 um.

15. The method of claim 1, wherein the treating is performed with a transmembrane pressure between 1 psi and 15 psi greater on the first side than the second side.

* * * * *